US010875820B2

(12) United States Patent
Tijm et al.

(10) Patent No.: US 10,875,820 B2
(45) Date of Patent: Dec. 29, 2020

(54) CATALYST FOR CONVERTING SYNGAS TO MIXED ALCOHOLS

(71) Applicants: Peter J. Tijm, Longmont, CO (US); Rex R. Stevens, Grand Junction, TX (US); Frans Lodewijk Plantenga, Hoevelaken (NE)

(72) Inventors: Peter J. Tijm, Longmont, CO (US); Rex R. Stevens, Grand Junction, TX (US); Frans Lodewijk Plantenga, Hoevelaken (NE)

(73) Assignee: Standard Alcohol Company of America, Inc., Denver, CO (US)

( * ) Notice: Subject to any disclaimer, the term of this patent is extended or adjusted under 35 U.S.C. 154(b) by 0 days.

(21) Appl. No.: 15/075,809

(22) Filed: Mar. 21, 2016

(65) Prior Publication Data

US 2016/0200647 A1 Jul. 14, 2016

Related U.S. Application Data

(63) Continuation-in-part of application No. 14/307,173, filed on Jun. 17, 2014, now Pat. No. 9,290,425.

(60) Provisional application No. 61/837,413, filed on Jun. 20, 2013.

(51) Int. Cl.
| | |
|---|---|
| *B01J 23/64* | (2006.01) |
| *C07C 29/156* | (2006.01) |
| *B01J 27/051* | (2006.01) |
| *B01J 37/20* | (2006.01) |
| *B01J 23/887* | (2006.01) |
| *B01J 37/03* | (2006.01) |
| *B01J 37/00* | (2006.01) |
| *B01J 23/74* | (2006.01) |
| *B01J 23/28* | (2006.01) |
| *B01J 23/22* | (2006.01) |

(52) U.S. Cl.
CPC ......... *C07C 29/156* (2013.01); *B01J 23/8877* (2013.01); *B01J 27/0515* (2013.01); *B01J 37/0036* (2013.01); *B01J 37/031* (2013.01); *B01J 37/20* (2013.01); *Y02P 20/52* (2015.11)

(58) Field of Classification Search
CPC ........ B01J 23/8877; B01J 23/74; B01J 23/28; B01J 23/22; B01J 27/0515; Y02P 20/52

USPC .................................................. 502/220, 221
See application file for complete search history.

(56) References Cited

U.S. PATENT DOCUMENTS

| | | | |
|---|---|---|---|
| 2,946,738 A | 7/1960 | Gardner et al. | |
| 3,720,602 A | 3/1973 | Riley et al. | |
| 4,122,110 A | 10/1978 | Sugier et al. | |
| 4,177,202 A | 12/1979 | Chang et al. | |
| 4,444,908 A | 4/1984 | Hass | |
| 4,513,100 A | 4/1985 | Fattore et al. | |
| 4,540,714 A * | 9/1985 | Pedersen | C07C 1/02 518/714 |
| 4,628,113 A | 12/1986 | Current | |
| 4,752,622 A | 6/1988 | Stevens | |
| 4,752,623 A * | 6/1988 | Stevens | B01J 23/85 502/206 |
| 4,831,060 A | 1/1989 | Stevens et al. | |
| 4,825,013 A | 4/1989 | Quarderer et al. | |
| 4,840,931 A | 6/1989 | Miller | |
| 4,882,360 A | 11/1989 | Stevens | |
| 5,663,455 A | 9/1997 | Harris et al. | |
| 6,235,677 B1 | 5/2001 | Manzer | |
| 6,319,872 B1 | 11/2001 | Manzer et al. | |
| 7,229,548 B2 | 6/2007 | Riley et al. | |
| 2005/0090688 A1 | 4/2005 | Hagiya | |
| 2010/0210741 A1 | 8/2010 | Kharas | |
| 2010/0331581 A1 | 12/2010 | Kharas | |
| 2011/0319505 A1 | 12/2011 | Janbroers et al. | |
| 2013/0029841 A1 | 1/2013 | Ferrari et al. | |
| 2013/0158300 A1* | 6/2013 | Wollrab | C07C 29/149 568/885 |

FOREIGN PATENT DOCUMENTS

| | | |
|---|---|---|
| CN | 1569331 | 1/2005 |
| EP | 0388070 A1 | 9/1990 |
| WO | 8503073 A1 | 7/1985 |
| WO | 0010698 A2 | 3/2000 |
| WO | 2009009389 A2 | 1/2009 |
| WO | 2012134490 A1 | 10/2012 |

* cited by examiner

*Primary Examiner* — Patricia L. Hailey
(74) *Attorney, Agent, or Firm* — O'Connor & Company; Ryan P. O'Connor

(57) ABSTRACT

Higher mixed alcohols are produced from syngas contacting a catalyst in a reactor. The catalyst has a first component of molybdenum or tungsten, a second component of vanadium, a third component of iron, cobalt, nickel or palladium and optionally a fourth component of a promoter. The first component forms alcohols, while the vanadium and the third component stimulates carbon chain growth to produce higher alcohols.

6 Claims, No Drawings

CATALYST FOR CONVERTING SYNGAS TO MIXED ALCOHOLS

This application claims the benefit of parent application Ser. No. 14/307,173, filed Jun. 17, 2014, which claims the benefit of provisional application Ser. No. 61/837,413, filed Jun. 20, 2013.

FIELD OF THE INVENTION

The present invention relates to catalysts for the production of mixed alcohols from synthesis gas, as well as to precursors of such catalysts and the use of the catalysts.

BACKGROUND OF THE INVENTION

Synthesis gas, or syngas, is made up of hydrogen ($H_2$) and carbon monoxide (CO) and may contain some carbon dioxide ($CO_2$) (and may contain other components as well). Syngas is available from a variety of sources, such as reforming natural gas, coal-bed gas or naphtha, from the gasification of coal, biomass, carbon rich materials, municipal wastes, etc. Using the well-known Fischer-Tropsch process, the syngas is passed over a catalyst and converted to hydrocarbons. When used to produce mixed alcohols, the process is a modified Fischer-Tropsch process and is generally referred to as Mixed Alcohol Synthesis (MAS). Stevens, U.S. Pat. Nos. 4,752,622, 4,752,623 and 4,831,060 disclose MAS catalysts and processes.

Mixed alcohols range from methanol ($C_1$—OH), ethanol ($C_2$—OH), propanol ($C_3$—OH) on up. Alcohols of $C_3$, $C_4$, etc. are referred to as higher alcohols. In general, higher alcohols are preferred for their higher BTU content over the lower alcohols of $C_1$ and $C_2$. In addition to the higher BTU content, higher alcohols have a lower volatility due to the longer hydrocarbon chain connected to the OH group.

On its face, the Stevens '622 patent seems promising in disclosing yields of higher alcohols. However, in practice, these results have not been replicated despite numerous attempts. It is desired to produce greater yields of the higher alcohols from the Fischer-Tropsch process in a repeatable manner. There are however reproducible data from Stevens '622 patent catalyst formula producing alcohols comprising 28-53 percent by weight methanol, 39-47% weight ethanol, 6-14% weight propanol, 0.7-3% weight butanol, and 0-2% weight pentanol.

We have found that using vanadium in the catalyst increases the yield of higher alcohols in a repeatable manner. In the prior art, it is known to use the Fischer-Tropsch process to make hydrocarbons, Miller, U.S. Pat. No. 4,840,931. The catalyst has a transition metal taken from the group of cobalt, molybdenum and vanadium. The metals are oxides. The current invention, however, uses metal sulphides.

In Quarderer, U.S. Pat. No. 4,825,013, the Fischer-Tropsch process is used to synthesize mixed alcohols, not hydrocarbons. The cobalt molybdenum catalyst is on a support. While the support may contain vanadium, the catalyst does not.

In addition to the design and makeup of the catalyst itself, attention is paid to the fabrication of the catalyst. Current practice for fabricating catalysts, and particularly catalysts that are sulfided for the reaction process, require great care be taken in protecting the catalyst from components in the air, such as oxygen. For example, bulk cobalt-molybdenum-sulfide based catalysts are very suitable for the production of alcohols, including mixed alcohols, from synthesis gas. Most catalyst synthesis routes are based on reactions using ammonium tetrathiomolybdate (($NH_4)_2MoS_4$) as a raw material and a sulfur source in the presence of hydrogen. Due to the air-sensitivity of the catalysts obtained, subsequent process steps in the production of the catalysts, like shaping and calcination need to be carried out under inert conditions.

On a commercial scale, protecting the catalyst from the atmosphere is expensive and time consuming. Additionally such sulfided catalysts are pyrophoric and, hence, present environmental concerns because of the starting materials employed. In the prior art, Janbroers, U.S. Pat. No. 8,980,782 recognizes this and discloses a technique to sulfide the catalyst in the reactor vessel. However, the Janbroers catalyst is very different.

A need thus persists for improved mixed alcohol synthesis catalysts, including vanadium, as well as improved processes for their production and use.

SUMMARY OF THE INVENTION

A modified Fischer-Tropsch catalyst for the synthesis of mixed alcohols from syngas, comprising a first component with at least one element selected from the group consisting of molybdenum or tungsten in free or combined form; a second component comprising vanadium in free or combined form; a third component with at least one element selected from the group consisting of iron, cobalt and nickel in free or combined form; and a fourth promoter component comprising an alkali or alkaline earth element in free or combined form.

In one aspect, the first, second, third and fourth components are supported on a carrier, which carrier is inert in the synthesis of mixed alcohols.

In still another aspect, the catalyst is a bulk catalyst.

In another aspect, the first component comprises crystalline molybdenum sulfide with a concentration in the catalyst is 33-43%, by weight, and the concentration of vanadium is 2-14%, by weight, among the molybdenum sulfide, the second component and the third component.

In still another aspect, the fourth promoter component comprises zirconium in free or combined form.

In still another aspect, the second component comprises vanadium sulfide.

In still another aspect, the first component comprises crystalline molybdenum sulfide with a concentration in the catalyst is 3-43%, by weight; the second component comprises vanadium sulfide, the concentration of vanadium is 2-14%, by weight, among the molybdenum sulfide, the vanadium sulfide and the third component; the fourth promoter component comprises zirconium in free or combined form.

A process of establishing a catalyst for producing a mixture of alcohols from a syngas, comprises the steps of providing a catalyst precursor, the catalyst precursor comprising molybdenum, cobalt and vanadium; locating the catalyst precursor in an interior of a reactor; closing the reactor to the atmosphere; providing a hydrogen agent in the reactor interior and pressurizing said reactor interior to 250-5,000 psig and heating the reactor interior and the catalyst precursor. A sulfiding agent is passed over the catalyst precursor wherein the catalyst precursor forms a sulfided catalyst, the sulfided catalyst comprising molybdenum sulfide, cobalt sulfide and vanadium sulfide. Syngas is passed over the sulfided catalyst in the reactor, the syngas comprising an amount of hydrogen to carbon monoxide of at least 0.5 hydrogen to 5.0 of carbon monoxide; and mixed alcohols are produced.

In one aspect, the sulfided catalyst comprises crystalline molybdenum sulfide, crystalline cobalt sulfide and vanadium sulfide in a reactor, with the following amounts by weight:

| | |
|---|---|
| molybdenum | 33-43% |
| vanadium | 2-14% |
| cobalt | 14-16% | among the molybdenum sulfide, cobalt sulfide and vanadium sulfide.

In another aspect, the alcohol distribution of the mixed alcohols is comprised of 17 to 31 weight (wt) % methanol, 39-49 wt % ethanol, 19 to 29 wt % propanol, 4 to 12 wt % butanol, 0.1 to 5 wt % pentanol, the balance being 0 to 10 wt % hexanol, heptanol, octanol, nonanol, decanol, ethers, esters and hydrocarbons.

DESCRIPTION OF THE PREFERRED EMBODIMENTS

The invention described herein uses an improved catalyst in a "modified Fischer-Tropsch synthesis process" for producing mixed alcohols. The catalyst is made up of various components, including vanadium. A promoter, such as of zirconium, can be used as well. The catalyst increases the yields of higher alcohols, while producing little or no hydrocarbons (such as gasoline, paraffins or waxes).

The catalyst is formed or established in several steps. A catalyst precursor is formed initially. The catalyst precursor is not sensitive to contact with the atmosphere and the oxygen contained in the atmosphere. The catalyst precursor is located in a reactor, which reactor is then closed to the atmosphere. The catalyst precursor is sulfided inside the reactor. The same reactor is then used to produce the mixed alcohols as syngas is passed over the sulfide catalyst in the reactor.

As an alternative, the catalyst can be sulfided ex situ. The sulfided catalyst is isolated from oxygen. One technique for isolating the sulfided catalyst is to immerse the catalyst in oil. Another technique immerses the sulfided catalyst in gas, such as nitrogen. The isolated, sulfided catalyst is then transported to the reactor and installed therein. The isolation material is removed from around the catalyst.

The modified Fischer-Tropsch process and a catalyst for making mixed alcohols are discussed in detail in Stevens, U.S. Pat. Nos. 4,752,622, 4,752,623 and 4,831,060. The Stevens patents disclose that the catalyst does not contain vanadium and/or zirconium and even that vanadium does not significantly alter the character of quantity of the alcohol fraction. It has now surprisingly been found that, contrary to Stevens' disclosure, vanadium in the catalyst composition does unexpectedly and materially contribute to the character and quantity of the alcohol fraction.

The catalyst includes the following:
a first component having at least one element selected from the group consisting of molybdenum and tungsten in free or combined form;
a second component of vanadium in free or combined form;
a third component having at least one element selected from the group consisting of cobalt, iron and nickel in free or combined form;
a fourth component being a promoter comprising an alkali or alkaline earth element in free or combined form.

As an option, a support can be used.

We believe that the first component forms alcohols, and the third component grows the carbon chains to longer or higher alcohols. We also believe that the second component, particularly when replacing or substituting for the first also stimulates or grows the carbon chains to longer or higher alcohols.

Describing now the components of the catalyst, the first component of the catalyst preferably consists essentially of at least one element selected from the group consisting of molybdenum and tungsten in free or combined form. Molybdenum is preferred. The molybdenum can be present as crystalline molybdenum sulfide or metallic molybdenum.

The first component of the catalyst may be present in the catalyst in "free or combined form" which means that it may be present as a metal, an alloy or a compound of the element. Representative compounds include the sulfides, carbides, oxides, halides, nitrides, borides, salicylides, oxyhalides, carboxylates such as acetates, acetyl acetonates, oxalates, etc., and the like. Representative compounds also include the elements in anionic form such as molybdates, phosphomolybdates, tungstates, phosphotungstatcs, and the like, and include the alkali, alkaline earth, rare earth and actinide series salts of these anions. The sulfides, carbides and oxides are preferred with the sulfides being most preferred for production of alcohols.

The molybdenum or tungsten may be present in an amount based on the weight of the total catalyst of at least about two percent, preferably at least about 5 percent with an upper limit of about 70 percent and preferably about 37 percent of the catalyst (without promoter or support).

The second component of the catalyst is vanadium, in metallic or combined form, which for the latter means that it may be present as a compound of the element and in particular as the sulfides.

The vanadium may be present in the amount based on the weight of the unpromoted catalyst (having the first, second and third component, but not the fourth component or a support (fifth component)) of at least about 2.5 percent, with an upper limit of 15 percent and preferably about 10 to 14 percent of the unpromoted catalyst. In general, the vanadium substitutes for some of the first component. That is to say, as the amount of vanadium increases, the amount of the first component decreases. The vanadium can be present as crystalline vanadium sulfide or metallic vanadium.

The third component of the catalyst preferably consists essentially of at least one element selected from the group consisting of iron, cobalt or nickel, or palladium in free or combined form. Cobalt is preferred.

The third component of the catalyst may be present in the catalyst in "free or combined form" which means that it may be present as a metal, an alloy or a compound of the element. Representative compounds include the sulfides, carbides, oxides, halides, nitrides, borides, salicylides, oxyhalides, carboxylates such as acetates, acetylacetonates, oxalates, etc., and the like. Representative compounds also include the elements combined with first component elements in anionic form such as iron, cobalt or nickel molybdates, phosphomolybdates, tungstates, phosphotungstates, and the like. The sulfides, carbides and oxides are preferred with the sulfide being most preferred for production of alcohols. The cobalt can be present as crystalline cobalt sulfide or metallic cobalt.

Although the various components can be in present in crystalline form, the sulfides components typically lack well defined crystals and polycrystalline.

The cobalt, iron or nickel or mixtures thereof may be present in an amount based on the weight of the total catalyst of at least about two percent, preferably at least about 5 percent with an upper limit of about 70 percent and preferably about 14-16 percent of the unpromoted catalyst.

The first and third components may be present in the finished catalyst in an atomic ratio of about 1:10 to about 10:1. Preferably the first and third components are present in a ratio of about 2:1 to 3:1. The first and second components may be present in the finished catalyst in an atomic ratio of about 20:1 to 2.5:1.

The fourth component, which is a promoter, may consist essentially of one or more alkali elements or alkaline earth elements in free or combined form. Alkali elements include lithium, sodium, potassium, rubidium and cesium. Alkaline earth elements include: beryllium, magnesium, calcium, strontium and barium. Alkali elements and in particular, cesium and potassium, are preferred. Potassium is most preferred. The promoter can comprise potassium carbonate, zirconium oxide and zirconium sulfide. The zirconium can be in free or combined form.

The promoter may be present in free or combined form as a metal, oxide, hydroxide, carbonate, sulfide or as a salt or a combination of these.

The alkaline promoter is preferably present at a level sufficient to render the supported catalyst or the bulk catalyst more basic. The promoter is generally present in an amount of at least about 0.05 weight percent as a free element in the finished catalyst. Preferably it is present in an amount of at least about 0.5 percent and most preferably at least 2.0 percent. Large amounts up to about 30 percent of the promoter may be present. Preferably the promoter is present at less than 20 percent.

The promoter may be added as an ingredient to the other components or to the support or may be part of one of the other components such as sodium or potassium molybdate or as an integral part of the support. For example, carbon supports prepared from coconut shells often contain small amounts of alkali metal oxides or hydroxides or the support may contain a substantial amount of the promoter such as when the support is magnesia.

The catalyst may be in bulk form, wherein the materials forming the catalyst provide physical structure and support. The bulk catalyst can be put into bulk form prior to sulfiding.

As an alternative to a bulk catalyst, a fifth optional component of the catalyst is a support, which may assume any physical form such as pellets, granules, beads, extrudates, etc. The supports may be coprecipitated with the active metal species, or the support in powder form may be treated with the active metal species and then used as is or formed into the aforementioned shapes, or the support may be formed into the aforementioned shapes and then treated with the active catalytic species.

The first three components may be dispersed on the support by methods known in the art. Examples include: impregnation from aqueous or non-aqueous solution followed by conversion to the active species, vapor deposition, intimate physical mixing, sulfiding of either first and/or second component species, precipitation of sulfides in the presence of the support and the like. One or more of these methods may be used.

One alternative method of placing the first four components on the support is known as the incipient wetness technique. Water- or solvent-soluble salts of the metals to be dispersed on the support are chosen. The soluble salts which may be a single salt or more than one salt are dissolved in a quantity of solvent which may be aqueous, nonaqueous or a mixed solvent. A sufficient quantity of the resulting solution is added to the support in an amount no more than will be completely absorbed by the support. The solvent is then evaporated to leave the salt dispersed on the support. Depending on the solubility of the salt chosen and on the quantity of the element desired to be dispersed on the support, this process may be performed once or several times. Impregnations with two or more species may be performed by codissolving them in the solvent or by adding them separately in different quantities or types of solvent. If the species loaded on the support is not the desired one, the loaded support may be treated to convert it to the desired species. For example, oxides may be reduced, with reducing agents such as hydrogen; salts may be decomposed for example by heating, for example, the decomposition of $(NH_4)_2MoS_4$ to $MoS_3$ and/or $MoS_2$; or one species may be converted to another by contact with a chemical agent, for example sulfiding. A catalyst may be sulfided by contact with a sulfiding agent in the presence of hydrogen. Examples of suitable sulfiding agents are hydrogen sulfide ($H_2S$), dialkylsulfides, dialkyldisulfides, alkyl polysulfide, and mercaptans. The presence of hydrogen is accomplished with a hydrogen agent such as hydrogen ($H_2$) or syngas, is made up of hydrogen and carbon monoxide (CO).

The most preferred methods of placing the components on a support include, for example, impregnation an aqueous mixture of the active metal salts, like (a) cobalt (hydroxy) carbonate or cobalt carbonate with (b) molybdenum oxide or molybdic acid and (c) vanadium acetate, followed by decomposition with heat to obtain the active metal oxides; after placing the components on a support it is preferably followed by treatment with $H_2$ at elevated temperatures, with $H_2S$ present in order to convert the metal oxides in active metal sulfides.

Other preferred methods of placing the first or second components on a support include, for example, impregnation with $(NH_4)_2MoS_4$ followed by decomposition with heat; precipitation of sulfides of the first and/or second components in contact with the support. Placing of the sulfided first and second components on a support is preferably followed by treatment with $H_2$ at elevated temperatures, usually with 20-100% $H_2S$ present, as described in Janbroers' U.S. Pat. No. 8,980,782, the entire disclosure of which is incorporated herein by reference.

Exemplary support materials include: the aluminas, basic oxides, the silicas, carbons, or suitable solid compounds of magnesium, calcium, strontium, barium, scandium, yttrium, lanthanum and the rare earths, titanium, zirconium, hafnium, vanadium, niobium, tantalum, thorium, uranium, and zinc. Oxides are exemplary compounds. The support can include cationic clays or anionic clays such as saponite, bentonite, kaolin, sepiolite or hydrotalcite, or mixtures thereof. Preferably the supports are neutral or basic or may be rendered neutral or basic by addition of the alkaline promoters. The aluminas include the alpha, gamma, and eta types. The silicas include for example, silica gel, silica-alumina, diatomaceous earth, and crystalline silicates.

The carbon supports, which are preferred supports, include activated carbons such as those prepared from coals and coal-like materials, petroleum-derived carbons and animal- and vegetable-derived carbons. Preferably the carbon support will have a surface area of 1-1500 $m^2/g$, more preferably 10-1000 $m^2/g$ and most preferably 100-500 $m^2/g$ as measured by the BET nitrogen test. Preferably, micropores (<20 Å (<2 nm)) are minimized and at least twenty percent of the volume of the pores comprises pores having a diameter of from about 20 Å to about 600 Å (2-60 nm). Examples include coconut shell charcoal, coals, petroleum cokes, carbons formed by pyrolyzing materials such as vinylidene chloride polymer beads, coal, petroleum coke, lignite, bones, wood, lignin, nut shells, petroleum residues, charcoals, etc.

Based upon the weight of the total catalyst, the support, when present, generally comprises at least about 10 percent of the catalyst and generally not more than about 96 percent of the catalyst.

For several reasons the preferred form of the catalyst is the agglomerated sulfide. Certain forms of cobalt/vanadium/molybdenum sulfide are more preferred. Most preferred is agglomerated, cobalt/vanadium/molybdenum sulfide in which the cobalt, vanadium and molybdenum sulfides are coprecipitated.

Methods for making sulfide catalysts are disclosed generally at pages 23-34 of *Sulfide Catalysts Their Properties and Applications*, O. Weisser and S. Landa, Pergamon Press, New York, 1973, the whole which is incorporated herein by reference.

Sulfide catalysts may be made by precipitating iron, cobalt or nickel sulfide in the presence of ammonium heptamolybdate or other thiomolybdates, or thiotungstates and thereafter thermally treating the mixture to convert the thiomolybdate or thiotungstate salt to the sulfide; or as disclosed in U.S. Pat. No. 4,243,553 and U.S. Pat. No. 4,243,554 which are hereby incorporated by reference; or from purchased active combined first and second component sulfides.

Cobalt and molybdenum may be impregnated as salts on a support, then calcined to the oxide and then sulfided with $H_2S$ as taught in GB patent publication No. 2,065,491 which is incorporated herein by reference. A cobalt/molybdenum sulfide may also be precipitated directly on to a support, but the unsupported cobalt/molybdenum sulfide is preferred. Other combinations of first and second component sulfides may be similarly made.

An unsupported catalyst preferably has a surface area of at least 10 $m^2/g$ and more preferably more than 20 $m^2/g$ as measured by the BET nitrogen surface area test.

A preferred method of making a cobalt/vanadium/molybdenum sulfide or other first through third component sulfide is by adding solutions of ammonium heptamolybdate or other equivalent salt, ammonium metavanadate and a cobalt or nickel salt such as the acetate more or less simultaneously to 30 percent acetic acid. This results in the coprecipitation of cobalt/vanadium/molybdenum sulfide. By varying the ratios of cobalt, vanadium and molybdenum or other salts in the solutions one may vary the ratio of cobalt and molybdenum or other elements in the sulfide catalyst. The cobalt/vanadium/molybdenum sulfide or other sulfide may then be separated from the solvent, dried and blended with a fourth component promoter such as $K_2CO_3$ and agglomerating agents and/or pelleting lubricants, then pelleted or extruded and used as the catalyst in the process.

The alkali or alkaline earth promoter may be added to the active catalytic elements prior to, during or after the formation of the sulfide by physical mixing or solution impregnation. The active metal sulfide may then be combined with binders such as bentonite clay, and/or pelleting lubricants such as Sterotex® and formed into shapes for use as a catalyst.

The finished catalyst may be used in a fixed bed, moving bed, fluid bed, slurry bed, ebullated bed or a graded bed wherein concentration and/or activity of the catalyst varies from inlet to outlet in similar manner to known catalysts. The catalyst may be used in powdered form or may be formed into shapes with or without a binder.

The catalyst can be established in the mixed alcohol reactor and sulfided in situ so as to prevent the sulfided catalyst from contacting the atmosphere. The catalyst precursor is formed, which precursor is not sulfided. As discussed above, the catalyst precursor can be in bulk form or located on a support. Once the catalyst precursor is formed, it is located inside the reactor. The catalyst precursor is located inside the reactor interior in the same manner as the catalyst will be used to make mixed alcohols. For example, if the syngas is passed through tubes of catalyst beads or pellets, then the beads or pellets of the catalyst precursor are likewise contained in the tubes. The catalyst precursor is contained within the tubes by retainers, such as quartz wool, glass beads and sintered metal mesh. An example of a catalyst located in tubes is shown in Tijm, U.S. Pat. No. 8,921,431, the entire disclosure of which is incorporated herein by reference.

Once the catalyst precursor is located in the reactor, the reactor is closed to the atmosphere. Then, the reactor is brought up to pressure and temperature for sulfiding the catalyst. The reactor contains a hydrogen agent such as $H_2$ or syngas during sulfiding. The hydrogen agent is in gas form for the sulfiding. Temperatures for sulfiding range between 250-375 degrees C. Pressures are between 100-2000 psig. Then, a sulfiding agent is passed over the catalyst precursor wherein the catalyst precursor forms a sulfided catalyst. $H_2S$ can be used to sulfide the catalyst. Sulphur is passed over the catalyst precursor for the desired amount of time, after which the catalyst has been sulfided. The sulfide catalyst contains molybdenum sulfide, cobalt sulfide and vanadium sulfide. The same reactor is used to produce mixed alcohols.

To produce mixed alcohols, syngas is fed to a reactor, which reactor has the catalyst. Syngas ratios for the feedstock are 0.1 to 10 of hydrogen to carbon monoxide. As an alternative, the hydrogen to carbon monoxide ratio is 0.5 to 5.0. As still another alternative, the hydrogen to carbon monoxide ratio is 0.75 to 2.5. It is believed that a feedstock ratio of 1:1 of hydrogen to carbon monoxide is preferred, as too much hydrogen is a chain terminator. Thus, the higher the hydrogen partial pressure and number of hydrogen molecules on the surface of the catalyst, the faster the growing molecules will terminate and become the synthesis product. Feedstock flows are 1,000 to 50,000 liters of syngas per hour per kilogram of crystalline molybdenum sulfide, crystalline cobalt sulfide and crystalline vanadium sulfide. As an alternative, feedstock flow is 1,000 to 25,000 liters per hour per kilogram. As still another alternative, feedstock flow is 2,000 to 15,000 liters per hour per kilogram.

The reactor is operated at pressures ranging from 250-5,000 psig. As an alternative, the pressure is 500-3,000 psig. The reactor is operated at temperatures ranging from 200-375 degrees Celsius. As an alternative, temperatures are 250-380 degrees Celsius and as still another alternative, 275-360 degrees Celsius.

The reactor and its catalyst form a single reaction zone. The syngas is passed through the reactor and in contact with the catalyst. Products exit the reactor. The reactor products need only pass through the reaction zone once and need only pass through one reaction zone. The efficiency of the catalyst is such that only one pass and one reaction zone is needed. Using a single reaction zone saves startup costs, as less reactor hardware is required. Using a single pass saves operational costs, as the throughput through the reactor is much higher with a single pass.

As an alternative to a single pass, the lower alcohols, such as methanol, from the reaction products can be fed back into the reactor for another pass in order to increase the yield of higher alcohols.

The mixed alcohols may include hexanol, heptanol, octanol, nananol and decanol. The reactor products exit the reactor and undergo separation. In addition to mixed alcohols, the reactor products include oxygenates, such as esters, ethers, ketones and hydrocarbons. These oxygenates need not be separated from the alcohols. Some syngas may pass through the reactor unconverted. The unused syngas can be separated and reused.

EXAMPLE 1

65 g of $(NH_4)_6Mo_7O_{24} \cdot 4H_2O$ (ammonium heptamolybdate) and 10 g of $NH_4VO_3$ (ammonium metavanadate) was added to 530 mL of $(NH_4)_2S$ (ammonium sulfide). The mixture was stirred and heated at 60-70 degrees C. for one hour. 50 minutes into the one hour, 470 mL of deionized water was added to the solution.

52.5 g of $Co(C_2H_3O_2)_2$ (cobalt acetate) was added to 600 mL of deionized water. This mixture was heated to 60 to 70 degrees C.

The two mixtures were then added to a baffled reactor that had been prepared by adding 700 mL of deionized water and 300 mL of acetic acid and heated to 60 degrees C. The two mixtures were added to the baffled reactor at equivalent rates. The mixture was held at 60 degrees C. for one hour in the reactor. A black precipitate formed. After allowing the precipitate to settle, excess liquid was removed and replaced with deionized water and the mixture was stirred and then allowed to precipitate again. The precipitate readily oxidizes when exposed to air, therefore care was taken to avoid this. The excess water was removed and replaced with acetone, and the mixture was allowed to precipitate.

The precipitate was then calcined by placing it in a kiln that had been purged with inert gas. The precipitate, or burden, was heated to 500 degrees C. and held for an hour.

Once calcined, the catalyst product was mixed with binder agents. Continuing with the example above, 86.5 g of catalyst were mixed with 26 g of bentonite and about 13 g of potassium carbonate. The mixture was put into a pebble mill for an hour to blend the contents. About 5 g of a pelleting lubricant such as Sterotex was added and the pebble mill was operated for five minutes. The catalyst was separated from the grinding media of the mill by screening. The catalyst was then ready for use.

In use, the catalyst was placed in a reactor. Syngas, having an $H_2$ to CO ratio of 1:1 was fed into the reactor at a temperature of 300-330 degrees C. and pressures of 1500-1540 psi. Conversions of both CO and $H_2$ were 38 to 42 percent. The measured mixed alcohols produced (% weight) are in TABLE 1:

TABLE 1

| | Example | | | | |
|---|---|---|---|---|---|
| | 1 | 2 | 3 | 4 | 5 |
| $C_1OH$ | 25-27% | 27-31% | 20% | 24% | 17% |
| $C_2OH$ | 46-49% | 39-44% | 45% | 48% | 39% |
| $C_3OH$ | 19-22% | 22-25% | 25% | 20% | 29% |

TABLE 1-continued

| | Example | | | | |
|---|---|---|---|---|---|
| | 1 | 2 | 3 | 4 | 5 |
| $C_4OH$ | 4-6% | 5-6% | 7% | 5% | 11% |
| $C_5OH$ | .39-.66% | .51-1.57% | 1.7% | 2.2% | 3.2% |
| $C_6OH$ | .02-1.9% | .03-.06% | 0% | 1% | .31% |

In addition to the $C_1$-$C_6$ alcohols, amounts of $C_7$-$C_{10}$ alcohols are also obtained.

EXAMPLE 2

The catalyst was prepared with the same components in the same manner as in EXAMPLE 1, except that 5 g of $NH_4VO_3$ was used, with a 5 g decrease in the molybdenum component.

The catalyst was placed in a reactor under the same operation conditions as in EXAMPLE 1. Conversion above CO and $H_2$ were 35 to 44%. The mixed alcohol results are given in TABLE 1.

EXAMPLE 3

The catalyst was prepared with the same components in the same manner as in EXAMPLE 1, except that 20 g of $NH_4VO_3$ was used, with a 20 g decrease in the molybdenum component.

The catalyst was placed in a reactor under the same operation conditions as in EXAMPLE 1. Conversion above CO and $H_2$ were 35-44%. The mixed alcohol results are given in TABLE 1.

EXAMPLE 4

The catalyst was prepared with the same components in the same manner as in EXAMPLE 1, except that 25 g of $NH_4VO_3$ was used, with a 25 g decrease in the molybdenum component.

The catalyst was placed in a reactor under the same operation conditions as in EXAMPLE 1. Conversion above CO and $H_2$ were 35-44%. These are also given in TABLE 1.

EXAMPLE 5

The catalyst was prepared with the same components in the same manner as in EXAMPLE 4, with 20 g of $NH_4VO_3$, with a 20 g decrease in the molybdenum component.

The catalyst was placed in a reactor under the same operating conditions as in EXAMPLES 1 and 4, except with a temperature increase to 340 degrees C. Conversion above CO and $H_2$ were 50-52%. These are also given in TABLE 1. The yields of higher alcohols were better than in EXAMPLE 4.

The component amounts (by weight) in the unpromoted catalyst are as follows:

| | |
|---|---|
| EXAMPLE 1 | 36.1% Mo |
| | 4.6% V |
| | 12.9% Co |
| EXAMPLE 2 | 42.3% Mo |
| | 2.5% V |
| | 14.1% Co |
| EXAMPLES 3 and 5 | 36.6% Mo |
| | 10.8% V |
| | 15.5% Co |

| EXAMPLE 4 | 33.9% Mo |
| | 13.8% V |
| | 15.8% Co |

In addition, another example catalyst uses the same components as in EXAMPLE 1, except that 15 g of $NH_4VO_3$ was used with 60 g of the molybdenum compound. The component amounts in the unpromoted catalyst are:
35.7% Mo
7.2 V
13.8 Co The concentration, by weight, of molybdenum in the catalyst, among the first, second and third components (the unpromoted catalyst), is between 33-43% and preferably between 36-43%. The concentration, by weight, of vanadium in the unpromoted catalyst is 2-14% and preferably 2-11%. The concentration, by weight, of cobalt in the unpromoted catalyst is 14-16% and preferably 15-16%.

The alcohol distribution comprises 7-31% methanol, 39-49% ethanol, 19-29% propanol, 14-22% butanol, 0.1-5% pentanol, the balance being 0-10% of $C_7$-$C_{10}$ alcohols (heptanol, octanol, nanonol, decanol) and ethers, esters and hydrocarbons, all by weight.

Thus, the yields of the higher alcohols $C_3$-OH to $C_6$-OH were about ¼ of the total. In addition, less methanol was produced than with prior art catalyst, with the remainder, almost ½, being ethanol. As can be seen, the yields of higher alcohols were higher.

Additional testing confirms the increase production of higher alcohols. A comparison was performed between two catalysts, both of which used molybdenum sulfide and cobalt sulfide. Catalyst A contained no vanadium. Catalyst B contained 10.8% vanadium sulfide, by weight. The operating conditions were identical, namely 1500 psig of pressure, temperature of 330 degrees C. and GHSV of 3800 to 4050. Catalyst A produced 53% methanol, 38% ethanol and 9% higher alcohols, by weight. Catalyst B, containing vanadium, produced 38% methanol, 50% ethanol and 11% higher alcohols, by weight.

The foregoing disclosure is merely illustrative of the principles of this invention and is not to be interpreted in a limiting sense.

That which is claimed is:

1. A modified Fischer-Tropsch catalyst for the synthesis of higher mixed alcohols from syngas, comprising:
   a) a first component comprises crystalline molybdenum sulfide;
   b) a second component comprising vanadium in free or combined form;
   c) a third component with at least one element selected from the group consisting of iron, cobalt and nickel in free or combined form;
   d) the molybdenum sulfide has a concentration in the catalyst of 33-43%, by weight among the molybdenum sulfide, the second component and the third component, and the concentration of vanadium is 2-14%, by weight among the molybdenum sulfide, the second component and the third component;
   e) a fourth promoter component comprising an alkali or alkaline earth element in free or combined form.

2. The modified Fischer-Tropsch catalyst according to claim 1, where the first, second, third and fourth components are supported on a carrier, which carrier is inert in the synthesis of mixed alcohols.

3. The modified Fischer-Tropsch catalyst of claim 1 wherein the catalyst is a bulk catalyst.

4. The modified Fischer-Tropsch catalyst of claim 1 wherein the fourth promoter component further comprises zirconium in free or combined form.

5. The modified Fischer-Tropsch catalyst of claim 1 wherein the second component comprises vanadium sulfide.

6. The modified Fischer-Tropsch catalyst of claim 1 wherein:
   a) the first component comprises crystalline molybdenum sulfide with a concentration in the catalyst is 33-43%, by weight;
   b) the second component comprises vanadium sulfide, the concentration of vanadium is 2-14%, by weight, among the molybdenum sulfide, the vanadium sulfide and the third component;
   c) the fourth promoter component comprises zirconium in free or combined form.

* * * * *